United States Patent [19]

Kurtz et al.

[11] Patent Number: 4,589,626
[45] Date of Patent: May 20, 1986

[54] HOSE CLAMP

[75] Inventors: Leonard D. Kurtz, Woodmere; Joseph LiCausi, Port Jefferson Station, both of N.Y.

[73] Assignee: BioResearch Inc., Farmingdale, N.Y.

[21] Appl. No.: 711,184

[22] Filed: Mar. 13, 1985

[51] Int. Cl.[4] ............................................. F16L 55/14
[52] U.S. Cl. ..................................... 251/10; 128/346
[58] Field of Search ................. 251/9, 10, 7; 128/346; 604/34

[56] References Cited

U.S. PATENT DOCUMENTS

| | | | |
|---|---|---|---|
| 2,804,092 | 8/1957 | Aitchison | 137/625.18 |
| 3,900,136 | 8/1975 | Paranto | 222/70 |
| 3,942,228 | 3/1976 | Buckman et al. | 251/4 |
| 4,097,020 | 6/1978 | Sussman | 251/10 |
| 4,235,412 | 11/1980 | Rath et al. | 251/10 |
| 4,346,869 | 8/1982 | MacNiell | 251/10 |
| 4,429,852 | 2/1984 | Tersteegen et al. | 251/9 |

*Primary Examiner*—Samuel Scott
*Assistant Examiner*—Allen J. Flanigan
*Attorney, Agent, or Firm*—Larson and Taylor

[57] ABSTRACT

A clamp for controlling the flow through a hose or flexible tubing such as is used in intravenous systems comprises a pair of parallel leg members joined by a curved end portion, each leg containing elements capable of clamping down on the tubing when the clamp is brought into closed position. The clamp contains a catch arm which sits on a flexible arm member at the free end portion of the clamp, and retains the upper leg member when the clamp is closed. Optionally, this catch arm can be multi-tiered, allowing the clamp to be closed at a variety of positions, each restricting a different amount of flow. When clamped, the clamping elements from each leg are alongside each other, crimping the tubing at two slightly separated points, and maximizing the clamping effect on the tubing. There are openings through the curved end portion and through the flexible arm member to receive the tube, and to retain it in position to maximize the effect of the clamp.

5 Claims, 8 Drawing Figures

HOSE CLAMP

FIELD OF THE INVENTION

This invention relates to a clamp for hoses or flexible tubing with upper and lower clamping elements to control flow through the tubing, and a protruding ledge to retain the clamp in closed position.

BACKGROUND OF THE INVENTION

Many small lightweight clamping devices capable of controlling flow through tubes employed in intravenous systems and the like are well known in the art. These clamps most commonly include those, such as U.S. Pat. No. 3,942,228, where protrusions extending from upper and lower limbs precisely coincide, pressing down on the same point of the tube in order to control flow. Other clamps, such as U.S. Pat. No. 4,235,412, employ a single protrusion on the lower limb, which fits between two protrusions on an upper limb in order to restrict flow.

It has been found that neither of these modes maximizes efficiency in cutting off the flow through these flexible tubes. It has been discovered that the maximization of fluid cut-off by a clamp will occur when the upper and lower protruding clamping elements do not precisely coincide, but end up alongside each other when the clamp is closed, as pressure is put on the tube at two slightly separate points.

SUMMARY OF THE INVENTION

It is thus an object of the present invention to provide a clamp which maximizes the control of liquids flowing through intravenous hoses or other flexible tubing.

It is also an object of the present invention to provide a clamp of simple construction which is easily clamped onto hoses or flexible tubing and easily released.

It is still further an object of the present invention to provide a clamp for hoses or flexible tubing which is durable, dependable, and easily manufactured.

These and other objects of the invention are achieved through a clamp with protruding clamping elements on upper and lower leg members of a U-shaped body, where the clamping elements are positioned one in front of the other, so that they impinge a flexible tube at two slightly separate points when the clamp is brought into closed position.

Other features and advantages of the present invention are stated in or will become apparent from the detailed description of the present invention found hereinbelow.

DETAILED DESCRIPTION OF THE DRAWINGS

Figure 1:
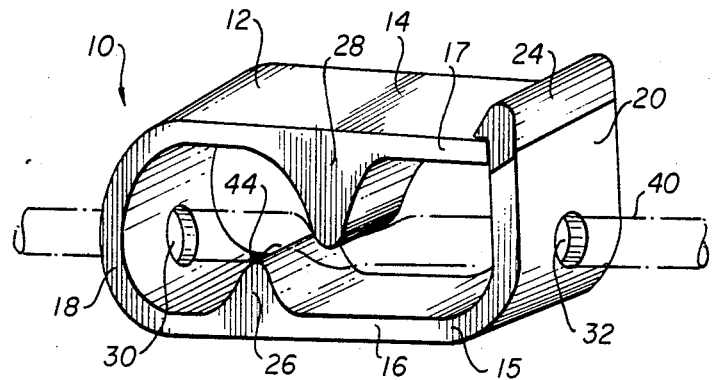
FIG. 1 is a perspective view of the clamp in closed position, with the hose or flexible tubing shown in phantom.

With reference to FIG. 1, the clamp 10 of the present invention comprises a body 12 of generally U-shaped configuration with approximately parallel upper and lower leg members 14 and 16, respectively, connected by a curved end portion 18. A flexible arm 20 extends upwardly from the rearward portion 15 of lower leg member 16 to a point below the upper leg member 14. The flexible arm member 20 has a catch arm 24 on its inner surface which acts as a catch member to retain the upper leg member 14 when the clamp is in a closed position, as observed in FIGS. 1 and 2. When clamped, the free end portion 17 of upper leg member 14 bears against catch arm 24.

Lower leg member 16 is provided with an upwardly extending clamping element 26 at the approximate midpoint of the lower leg member. The upper leg member 14 is provided with a downwardly extending clamping element 28 which is attached to the upper leg member at a position slightly forward of upwardly extending clamping element 26 when the clamp 10 is brought into the closed position. The downwardly extending clamping member 28 may be formed as part of the upper leg member (as shown in FIGS. 1–3) or can be constructed as a separate piece which is then attached to the upper leg member (configuration not shown).

Figure 2:
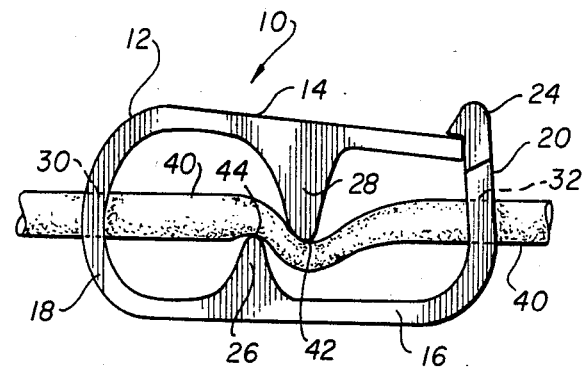
FIG. 2 is a side view of the clamp in closed position, with tubing in place.
Figure 3:
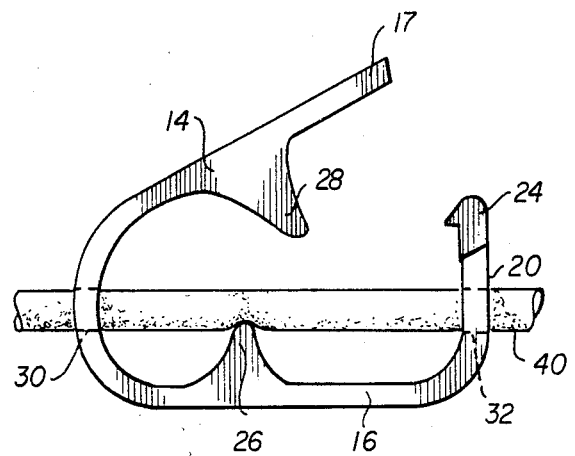
FIG. 3 is a side view of the clamp in open position, with tubing in place.

The curved end portion 18 of clamp body 12 is formed with a central opening 30 capable of receiving a hose or flexible tubing 40, as observed in FIGS. 1–3. The flexible arm member 20 also contains an opening 32 capable of receiving a hose or flexible tubing 40, which is aligned to receive tubing after it passes through opening 30 of curved portion 18 of the clamp. The hose or flexible tubing 40 is aligned via openings 30 and 32 so that it can be crimped by clamping elements 26 and 28 when the clamp is closed.

In operation, the clamp 10 is positioned on flexible tubing 40 by placing the tubing through openings 30 and 32 while the clamp is in open position, resulting in the configuration observed in FIG. 3. When it is desired to stop flow through the hose or flexible tubing 40, the upper leg member 14 is pressed toward lower leg member 16 so that the free end portion 17 of the lower leg member engages the catch arm 24 of flexible arm member 20. In this position, as observed in FIGS. 1 and 2 the clamping elements 26 and 28 impinge upon the hose 40 at two slightly separate points, 42 and 44, such that the tube is compressed along a contact area beginning at point 42 and extending upward and rearward, terminating when the left wall of member 28 and the right wall of member 26 begin to diverge. As a result, the hose is crimped to such an extent that the flow of fluid is completely halted.

It is desirable that the separation between clamping elements, for a clamp of approximately 1.75 inches in length, is about 0.100 inches, the approximate width of a flattened tube without compression. This separation of 0.100 inch refers to the approximate distance between the left wall of element 28 and the right wall of element 26 when the clamp is brought into closed position. It is also desirable that the two clamping elements overlap each other in order to create a "friction factor" against pulling the tube through while the clamp is closed. While the length of overlap for a precise "friction factor" is unknown, a 0.100 inch overlap has been effective with the 1.75 inch clamp.

In order to insure total close off of fluid or air flow through the tubing, it is necessary to compress the tube to approximately one-half of its non-compressed wall thickness. For a flattened tube of 0.100 inch width, effective flow cut-off occurs when the downwardly extending clamping element reaches a point aproximately 0.050 inches above the lower leg member. Thus, for proper compression, the distance between the downwardly extending clamping element and the lower leg member should be about 0.050 inches when the clamp is in closed position.

When it is desired that flow be resumed, the clamp is opened by pushing the flexible arm 20 away from the upper leg member 14 so that the free end portion 17 of the upper leg member is released, and the clamp resumes the open position, as seen in FIG. 3.

It is also desirable in certain cases to be able to allow an intermediate amount to flow through the tubing in an IV or other similar system. In order to control the flow such that fluid can be merely slowed down instead of shut off completely, the clamp of the present invention can be constructed with a multi-level catch arm. This catch arm has a plurality of protrusions, each capable of retaining the clamp in a different closed position, thus allowing one to cut off more or less flow as desired.

Figure 4:
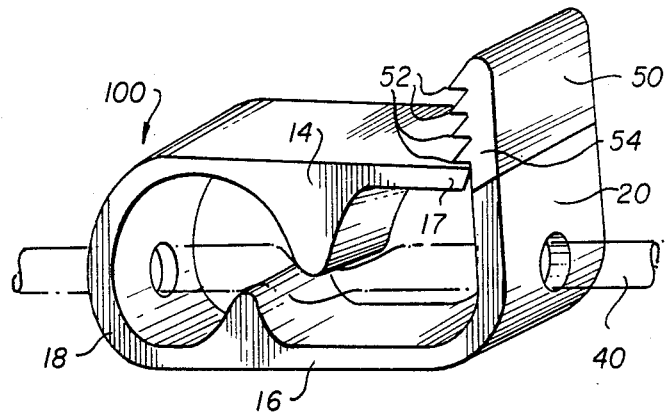
FIG. 4 is a perspective view of the clamp with a multi-leveled catch arm.

The clamp 100 with a multi-leveled catch arm 50 is observed in FIG. 4. In this embodiment of the invention, the multi-tiered catch arm 50 is found on the upper end of the flexible arm member 20. The catch arm consists of a plurality of ledges, shown generally as 52, each of which is capable of retaining the upper leg member 14 in a fixed position. For maximum cut-off, i.e., where no fluid can flow through the tube, the upper leg member 14 is brought to the lowermost ledge 54 of the multi-leveled catch arm 50, where it is retained, as observed in FIG. 4.

Figure 5:
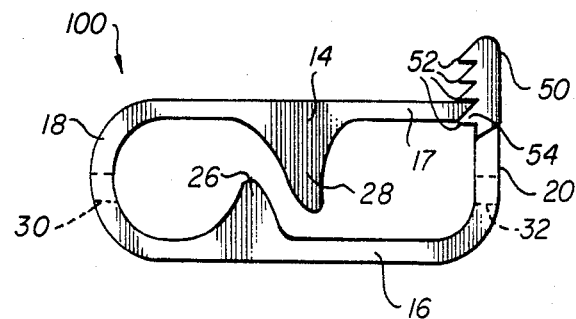
FIG. 5 is a side view of the clamp in FIG. 4 in intermediate closed position.
Figure 6:
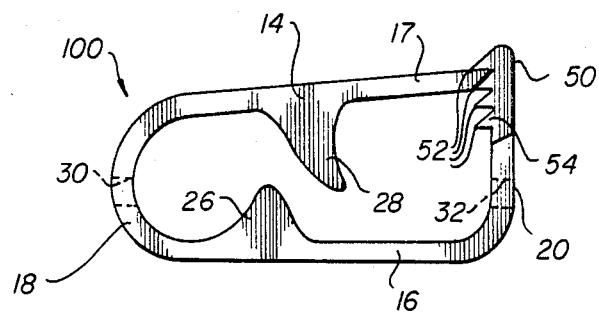
FIG. 6 is a side view of the clamp in FIG. 4 in another closed position.

When it is desired to allow some fluid to flow through the hose, the upper leg member 14 can be brought into a position by which it is retained by one of the ledges 52 above lowermost ledge 54. This is observed in FIG. 5 where the free end portion 17 of upper leg member 14 is retained by intermediate ledge 56 of the multi-leveled catch arm 50. In this position an intermediate amount of fluid (something less than maximum) will be allowed to flow through the tubing. For the least amount of restriction, the clamp will be closed so that upper leg member 14 is retained by the uppermost ledge 58 of the catch arm, as observed in FIG. 6.

Figure 7:
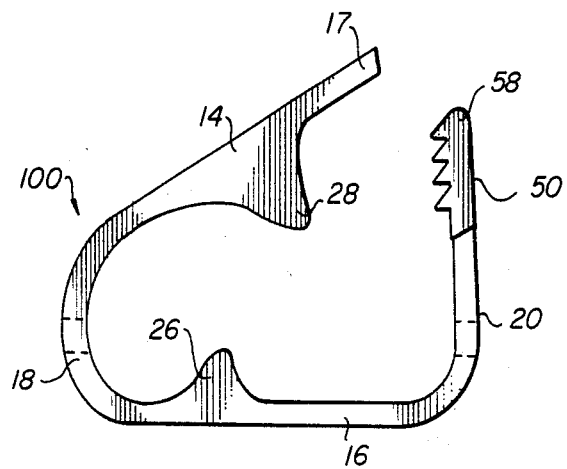
FIG. 7 is a side view of the clamp in FIG. 4 in open position.

When flow is to be entirely resumed, the upper leg member 14 is released by pushing flexible arm member 20 away from the free end portion 17 of the upper leg member. This allows the upper leg member to clear uppermost ledge 58 of the catch arm, and the clamp 100 now returns to the open position, as observed in FIG. 7.

Figure 8:
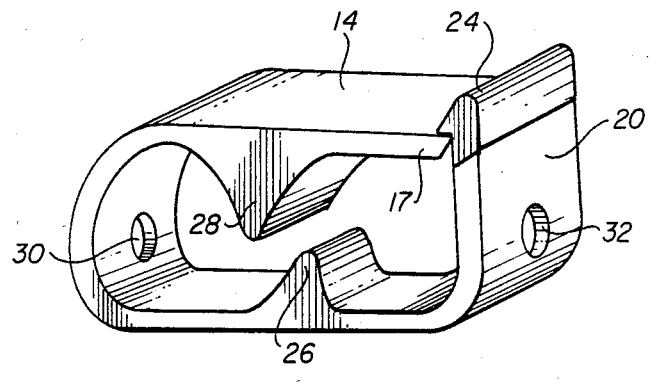
FIG. 8 is a perspective view of an alternative embodiment of the invention.

It is not essential that the top clamping element 28 be disposed slightly in front of the lower clamping element 26. Their relative positions can be reversed, and this configuration is observed in FIG. 8.

The clamp may be made of any material giving it the required flexibility as well as strength and durability. It is desirable, therefore, to make the clamp out of wear-resistant plastics. However, any suitable plastic or other material with similar strength and flexibility may be employed.

We claim:

1. A clamp for controlling flow through hoses or flexible tubing, said hoses or flexible tubing being positioned between two clamping elements which control flow through the hose or tubing, said clamp comprising a generally U-shaped body, having generally parallel upper and lower leg members connected by a curved end portion, one of said clamping elements extending upwardly from said lower leg member, the other extending downwardly from said upper leg member, one of said clamping elements located at a point on said clamp which is slightly forward of the other clamping element when the clamp is brought into closed position, said clamping elements disposed so that they overlap each other when viewed along the tubing axis when the clamp is closed in order to create friction against pulling the tube through the clamp, a flexible arm member extending upwardly from and forming approximately a right angle with the rearward end of the lower leg member and projecting beyond the upper leg member, a protruding ledge member located in said flexible arm member at a position approximately level with said upper leg member, capable of retaining the upper leg member when the clamp is brought to a closed position, said curved end portion having an opening capable of receiving a hose or flexible tubing, and said flexible arm member having an opening capable of receiving a hose or flexible tubing, said opening aligned with the opening in said curved end portion.

2. A clamp as claimed in claim 1 wherein the separation between clamping elements when the clamp is brought into closed position approximately equals the width of a flattened tube without compression in order to create friction against pulling the tube through the clamp when the clamp is closed.

3. A clamp as claimed in claim 1 wherein the amount of overlap of the two clamping elements approximately equals the width of a flattened tube without compression.

4. A clamp as claimed in claim 1 wherein the downwardly extending clamping element compresses a tube to approximately one-half of its noncompressed wall thickness when the clamp is closed in order to effect a total cut-off of flow through said tube.

5. A clamp as claimed in claim 1 where the catch arm comprises a plurality of ledges each capable of retaining the upper leg member, said ledges positioned sequentially along the upper end of said flexible arm member, the lowermost of said ledges capable of retaining said clamp in a position so as to cut off flow through said tubing entirely, and the remainder of said ledges positioned so as to retain said clamp in a position whereby some flow through said tubing is allowed, with progressively greater flow allowed as said clamp is retained by said ledges closer to the upper end of said flexible arm member.

* * * * *